United States Patent [19]
Bernstein et al.

[11] Patent Number: 5,501,112
[45] Date of Patent: Mar. 26, 1996

[54] RETRODICTIVE MOLECULAR AND PARTICLE IN-SITU SNARES

[75] Inventors: Ralph Bernstein, Los Altos; Vasu H. Tahiliani, San Jose; Mario Rabinowitz, Redwood City, all of Calif.; Richard Grace, Pittsburgh, Pa.

[73] Assignee: Electric Power Research Institute, Inc., Palo Alto, Calif.

[21] Appl. No.: 86,794

[22] Filed: Jul. 2, 1993

[51] Int. Cl.$^6$ ........................................ G01N 1/22
[52] U.S. Cl. .................... 73/864; 73/864.51; 73/864.63
[58] Field of Search ............... 73/863.21, 864.51, 73/863, 864, 864.63, 864.91, 864.31, 864.32, 863.91, 863.92, 23.21, 28.04, 31.02, 31.07

[56] References Cited

U.S. PATENT DOCUMENTS

| | | | |
|---|---|---|---|
| 3,430,482 | 3/1969 | Dravnieks et al. | |
| 3,987,677 | 10/1976 | Alter | 73/864.51 X |
| 3,998,101 | 12/1976 | Bradshaw et al. | 73/864 |
| 4,046,014 | 9/1977 | Boehringer | |
| 4,102,201 | 7/1978 | Trine et al. | 73/864 X |
| 4,111,049 | 9/1978 | Lerner et al. | 73/864 X |
| 4,166,379 | 9/1979 | Bradshaw | 422/88 X |
| 4,301,114 | 11/1981 | Rounbehler et al. | 422/52 |
| 4,348,888 | 9/1982 | Snee | 422/98 |
| 4,565,786 | 1/1986 | Dunkhase et al. | 73/864.51 X |
| 4,580,440 | 4/1986 | Reid et al. | 73/864 X |
| 4,685,880 | 8/1987 | Meguro et al. | 425/416 |
| 4,709,265 | 11/1987 | Silverman et al. | 73/863 X |
| 4,987,767 | 1/1991 | Corrigan et al. | 73/864 X |
| 5,092,218 | 3/1992 | Fine et al. | 73/1 G X |

FOREIGN PATENT DOCUMENTS

| | | | |
|---|---|---|---|
| 127689 | 9/1987 | Japan | 73/170.21 |
| 120366 | 1/1959 | U.S.S.R. | 73/864.51 |
| 1504546 | 8/1989 | U.S.S.R. | 73/864.51 |

OTHER PUBLICATIONS

*Patent Abstracts of Japan*: ABS Grp No. P833, ABS vol. No. 13, No. 253, ABS pub. date Jun. 13, 1989 (abstract of Japanese patent 01–50985 published Feb. 27, 1989 and entitled "Apparatus for Measuring Distribution of Number, Size, and Area of Snow Flake of Snowfall").

*Primary Examiner*—Thomas P. Noland
*Attorney, Agent, or Firm*—Townsend and Townsend and Crew

[57] ABSTRACT

Method and apparatus are presented for snaring explosive, combustible, and other hazardous compounds in vapor and in particulate form, and also combustion residues, which system can be used to prevent, or retrodict the cause of explosions, fires, etc. after they have occurred. The snares are in the form of gated chambers on rotating time disks and moving belts which are used to capture molecules and particulate matter. The combination detects hazardous molecules and combustible particles or causes of dust explosions; and indicates an approximate time-history record of the evolution of particles before or during the course of fires and explosions, or other onerous occurances.

5 Claims, 1 Drawing Sheet

RETRODICTIVE MOLECULAR AND PARTICLE IN-SITU SNARES

BACKGROUND OF THE INVENTION

1. Field of the Invention

Unexpected and unknown explosive, combustible, toxic and other hazardous gases and particles can be released from a number of disparate causes. It has been very difficult if not virtually impossible to determine which gases and/or particles caused a fire or explosion after the event, as the gases have been ignited and dispersed. If the culprit gases could be identified, this would be the first step in the prevention of such onerous processes. For example, in electric utility underground distribution networks, violent explosions have occurred in access areas, splice boxes, and underground vaults under manhole covers.

This invention pertains to a system of in situ snaring, trapping, or collection of gases and particles before and/or during an accident. This apparatus can be used to prevent or retrodict the cause of explosions, fires, etc. after they have occurred; or even prevent them when there is a slow build up of the hazardous gases by identifiying them before an accident. Said snares are in the form of rotating chambers in disks and hoop-belts to capture molecules and particulate matter. The device detects hazardous molecules and combustible particles; and gives a discrete time-history record of the evolution of particles before or during the course of fires and dust explosions, or other accidents.

Definitions

"Snare" as used here and in the claims refers to chambers which periodically are opened and closed to sample the surrounding gases and particles and to act as volatile vapor and particulate snares.

A "molecular snare" is a sealed off chamber which holds molecules sampled from the surrounding space including possible culprit molecules.

A "particle snare" is a sealed off chamber which holds particles sampled from the surrounding space including possible culprit particles. Such particles may sometimes be the cause of explosions as in dust explosions. Sometimes these particles are part of the debris from an explosion and their identification may help in retrodicting the cause of the explosion.

"Retrodiction" as a term used here refers to a retrospective process of deducing or inducing by analysis of the snared molecules and particles to move backwards from the gathered evidence and facts, to determine an earlier state or condition that led to the present state.

2. Description of the Prior Art

In U.S. Pat. No. 3,430,482 entitled *Automatic Bomb Detector* issued to Andrew Dravnieks et al on Mar. 4, 1969, a bomb detector is described for in situ use such as in an airplane. Although it and similar patents for a complete detection system are for in situ use, they are specifically directed at the detection of bomb materials, whereas our invention is more general. They are also not intended for retrodictive use.

In U.S. Pat. No. 4,046,014 entitled *Sealable Activated Charcoal Gas Sampler* issued to John Boehringer on Sep. 6, 1977, activated charcoal is used for sampling ambient gases. Its use does not relate to combustion and explosions. Nor is it intended for preventative and/or retrodictive applications to prevent or determine the cause of fires and explosions.

In U.S. Pat. No. 4,166,379 entitled *Apparatus for the Detection of Volatile Organic Substances* issued to Robert Bradshaw on Sep. 4, 1979, a complete apparatus is described for the detection or control of the flow of gases containing organic volatile substances.

In U.S. Pat. No. 4,301,114 entitled *Molecular Sieve Trap for Nitrogen Compound Detection,* issued to David P. Rounbehler et al on Nov. 17, 1981 an N-nitroso compound detection system is disclosed wherein a molecular sieve trap is interposed in a gas stream between a pyrolyzer and a chemiluminescent NO detector to selectively trap substances in the reactor effluent. Also disclosed is a $NO_x$ detection system having a molecular sieve trap in a sample inlet line of a $NO_x$ detector. The system is for use in a laboratory setting as a component of a complete laboratory detection apparatus system rather than in situ retrodictive use. In the gas stream, trapping in the molecular sieve is primarily flow dependent over a relatively short period of time, whereas in our application snaring is primarily time dependent over a substantially longer period of time.

U.S. Pat. No. 4,348,888 entitled *Explosimeter* issued to Timothy Snee on Sep. 14, 1982, describes a complete system for determining the concentration of combustible material as a function of the quantity of oxygen required for complete combustion. It is not a retrodictive system. It is also a much more expensive system than that of the instant invention.

U.S. Pat. No. 5,092,218 entitled *Selective Detection of Explosive Vapors* issued to David H. Fine et al on Mar. 3, 1992, describes a complete system in which a high speed gas chromatograph separates the vapors which are then analyzed. It is also a much more expensive system than that of the instant invention.

The prior art contains no in situ preventative and/or retrodictive capabilities for vapor and particulate identification as in the instant invention. It would be advantageous to have a rugged, inexpensive, self-contained device capable of surviving explosions that can achieve in situ preventive and/or retrodictive detection as well as time-history capability to record combustible or explosive compounds without the high cost, complexity, and explosion vulnerability of the prior art.

SUMMARY OF THE INVENTION

In accordance with the illustrated preferred embodiments, in situ apparatus is presented that is capable of determining the chemical composition of volatile compounds and particulate matter to prevent or retrodict combustion and explosions. An inexpensive, rugged, reusable device capable of surviving explosions snares or collects gases and particles from a surrounding space before or during an accident occurring in the space for later analysis in determining the cause of the explosion or other accident. This invention deals with the broad general concept of method and apparatus whereby molecular and particulate snares are provided which will hold and retain hazardous gases and particles. The snares can routinely be removed and inspected in laboratories to determine which gases are accumulating. If an explosion occurs, the chambers collecting the gases and particles can survive the explosion to be analyzed to determine the culprit gases.

Applications of this invention relate to a wide variety of potentially hazardous sites. They range from the detection of explosive gases produced from the deterioration or damage to high voltage or high current distribution lines, to the detection of explosive fuel gases or fumes in enclosed systems, and even the trapping of gases and particulates from a terrorist bomb explosion. Because of its ruggedness and inexpensiveness, it can be useful at a multitude of generation, and underground distribution and transmission sites, as well as at electric substations and other sites vulnerable to terrorist bombing. The objective of this invention is to provide a retrodictive historical record of the combustible gases that were present.

DETAILED DESCRIPTION OF THE PREFERRED EMBODIMENTS

Convention Regarding Reference Numerals

Figure 1:
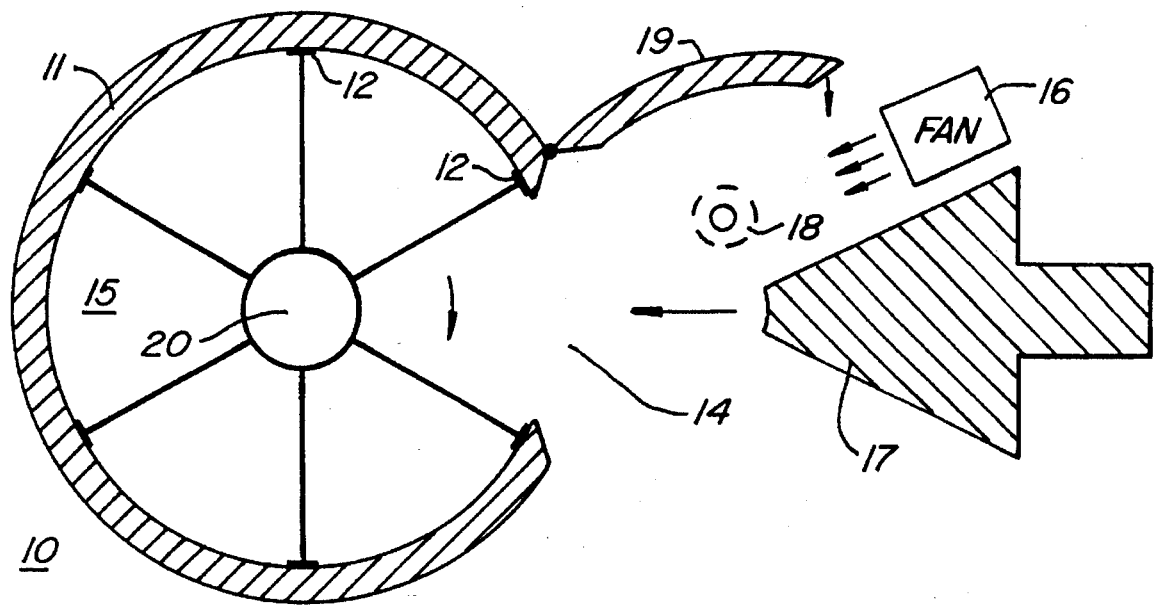
FIG. 1 is a cross-sectional schematic view of a time-history snare disk with chambers to snare molecules and particulates illustrating a purging-renewal system.

In the figures, the first digit of a reference numeral indicates the first figure in which is presented the element indicated by that reference numeral.

FIG. 1 is a cross-sectional schematic view of a time-history snare disk 10, having an outer casing 11, with sliding seals 12 and an opening 14 in the casing. The rotating disk with chambers has radial wedge shaped segment chambers 15 that are sealed off from each other to partition off sections of the disk as it rotates inside the casing 11. The disk can be made to rotate by a rotation means (not shown) such as a wound spring, compressed $N_2$ gas, or a sealed (to avoid sparking and ensuant explosion) electric motor. As the circumference of a chamber 15 comes into alignment with the opening 14, molecules and particulates enter the open chamber and beome snared as the chamber rotates into a closed position when the adjacent chamber becomes exposed. A fan 16 helps to circulate the air to the open chamber 15. A clock 20 or cycle-counter used in conjunction with this belt system or the wheel systems of the previous figures, gives precison to the time sequence of events.

The mechanical structure of the rotating chamber gas-particulate snare is similar to an enclosed rotating carousal that historically in time sequence captures sampled ambient gas-particles for later analysis. It retains them until released after a complete cycle. To facilitate the purging-renewal of the system, a piston 17 is pushed into each chamber 15 at the completion of a cycle prior to the next cycle. This can be accomplished mechanically by the piston displacement of the air chamber, or by a burst of fresh compressed gas successively as each chamber opens at the end of a cycle, or by evacuation. When there is a rise in pressure, a pressure transducer 18 such as a hot wire air flow and pressure sensor used in automobile engines causes a gate 19 to rapidly close the opening 14 to lock the gases and particles in the time-history snare disk 10. The gate 19 may take any of a number of forms, including a spring or an air driven guillotine gate structure for very rapid closing. Gating may not always be necessary, depending upon the pressure of the explosion and tightness of the seals 12.

The succession of snared gases and particles in each chamber can help to retrodict the course of their evolution leading to an undesired event such as fire or explosion. Prior to an untoward or onerous event, the disk assemblies are periodically removed and analyzed with laboratory apparatus such as optical or mass spectrometers; or a complete portable system. Following an accident, the disk contents can be analyzed to retrodict what had happened.

Figure 2:
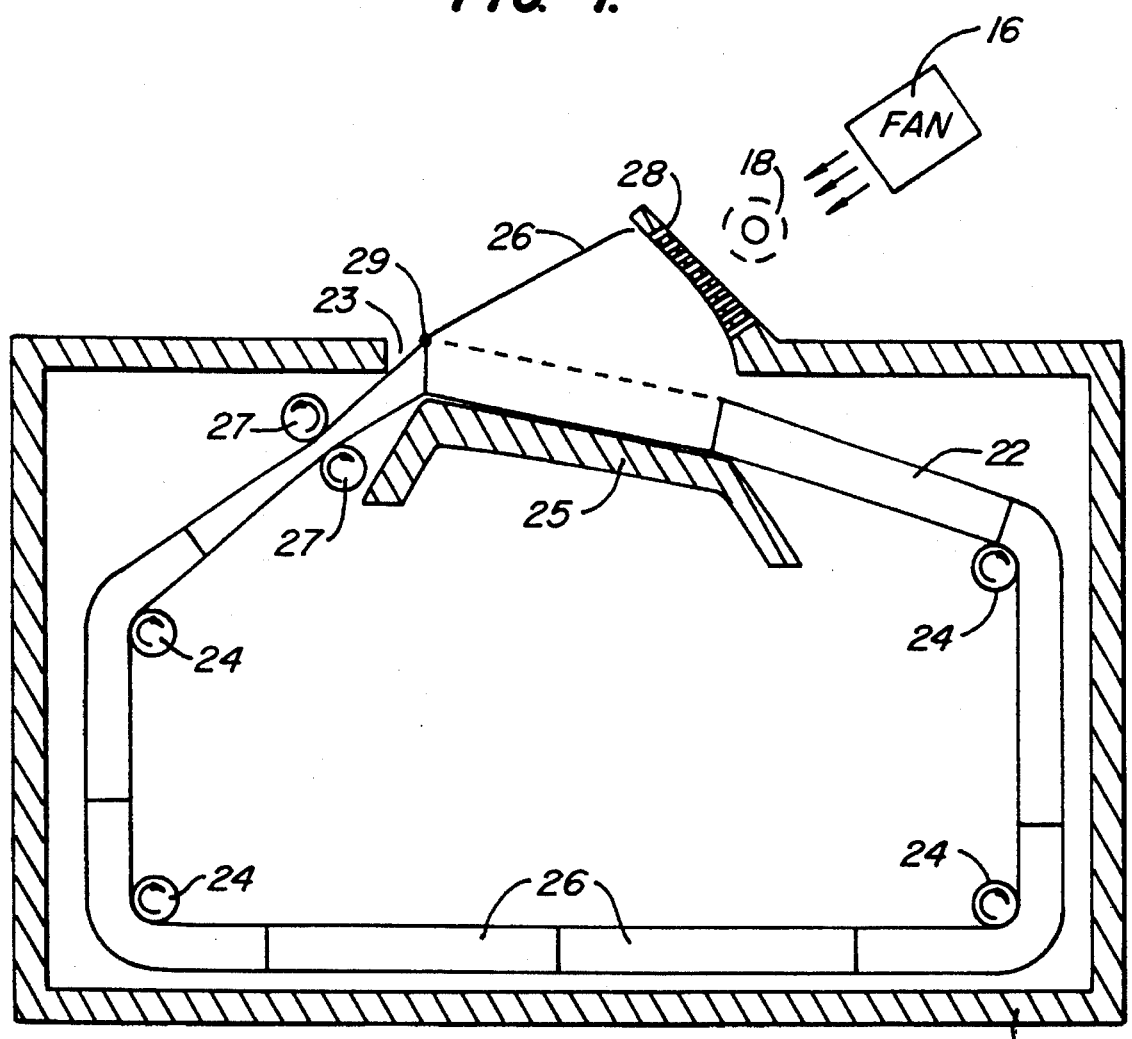
FIG. 2 is a cross-sectional view of a time-history continuous rotating belt-snare device illustrating a purging-renewal system.

FIG. 2 is a cross-sectional view of a time-history continuous rotating snare-belt device having a long continuous snare-belt 22 that has exposure outside of the opening 23, with the vast remainder of the belt folded around and moving over rollers 24 inside of a housing 25. The snare-belt 22 has individual chambers 26 that hold sampled gas. The belt is propelled by a rotation means (not shown) such as a wound spring, compressed $N_2$ gas, or a sealed (to avoid sparking and ensuant explosion) electric motor, and operates like a printer or typewriter chambered ribbon, and may similarly be rolled up on spools inside the housing 25. As a chamber 26 reaches the opening 23, a spring 29 loaded gate 26 opens exposing the open chamber to the ambient gases and particulates which enter the open chamber and beome snared when the door 26 closes due to contact with structural member 28 as the belt moves inside the housing 25 and the adjacent chamber becomes exposed. A fan 16 helps to circulate the air to the open chamber 26. Rollers 27 squeeze out the snared gas from a chamber 26 after each complete cycle, thus purging the chamber and renewing it for subsequent exposure. The contents of said flexible chambers may be expelled into the surrounding space or squeezed into a detection apparatus. A pressure transducer 18 such as a hot wire air flow and pressure sensor used in automobile engines can sense incipient changes to cause the device 20 to speed up, and to also put it in safeguard mode.

While the invention has been described with reference to preferred and other embodiments, the descriptions are illustrative of the invention and are not to be construed as limiting the invention. Thus, various modifications and applications may occur to those skilled in the art without departing from the true spirit and scope of the invention as summarized by the appended claims.

We claim:

1. Apparatus for collecting gases and particles from a surrounding space before and during an accident occurring in the space to permit the gases and particles to be later used to determine the cause of the accident, said apparatus comprising;

a hollow body having a wall provided with at least one opening, said body being in the space;

including a flexible belt movable through each opening, permitting the belt to move into and out of the body, there being means for moving the belt relative to the body, said belt having a multitude of flexible collection chambers, the chambers are rejuvenatable by being squeezed to force out the collected gases and particles.

2. Apparatus for collecting gases and particles as set forth in claim 1 wherein said belt has a multitude of collection chambers, and further comprising a gate which opens to expose a chamber and closes to seal a chamber.

3. A method of collecting gases and particles from a surrounding space before or during an accident occurring in the space so that the gases and particles can be used later in determining the cause of the accident, said method comprising:

providing a hollow body in the space;

moving a flexible belt relative to the body through an opining in a wall of the body;

causing the belt to move into and out of the body;

said belt having a multitude of flexible collection chambers; and rejuvenating said chambers, said rejuvenating step including squeezing each chamber to force out the collected gases and particles.

4. A method of collecting gases and particles as set forth in claim 3 wherein said belt has a multitude of flexible collection chambers, and squeezing the contents of the chambers into a detection apparatus.

5. A method of collecting gases and particles as set forth in claim 3, wherein said belt has a multitude of flexible collection chambers, opening a gate to expose a chamber, and closing the gate to seal the chamber.

* * * * *